United States Patent [19]

Meffert et al.

[11] 4,299,737

[45] Nov. 10, 1981

[54] STABLE AQUEOUS OR AQUEOUS-ALCOHOLIC SOLUTIONS OF FAT-SOLUBLE PERFUME OILS

[75] Inventors: Alfred Meffert; Fanny Scheuermann, both of Düsseldorf; Achim Werdehausen, Haan, all of Fed. Rep. of Germany

[73] Assignee: Henkel Kommanditgesellschaft auf Aktien, Düsseldorf-Holthausen, Fed. Rep. of Germany

[21] Appl. No.: 130,721

[22] Filed: Mar. 17, 1980

[30] Foreign Application Priority Data

Apr. 4, 1979 [DE] Fed. Rep. of Germany ....... 2913467

[51] Int. Cl.³ .............................................. C11B 9/00
[52] U.S. Cl. .............................. 252/522 R; 568/620; 568/624
[58] Field of Search .............................. 568/620, 624; 252/522 R

[56] References Cited

U.S. PATENT DOCUMENTS

| | | | |
|---|---|---|---|
| 3,022,335 | 2/1962 | Lundsted | 568/620 |
| 3,535,307 | 10/1970 | Moss | 568/624 |
| 3,954,884 | 5/1976 | Kidwell | 568/620 |
| 4,184,985 | 1/1980 | Schenermann et al. | 252/522 R |

*Primary Examiner*—John F. Niebling
*Attorney, Agent, or Firm*—Hammond & Littell, Weissenberger and Muserlian

[57] ABSTRACT

This invention relates to clear, stable aqueous or aqueous-alcoholic solutions of fat-soluble perfume oils which contain hydroxyalkylether alkoxylates as solubilizers. Said solubilizers are prepared by reacting epoxyalkanes with mono- or polyfunctional alcohols and then reacting the reaction product thereof successively with propylene oxide and ethylene oxide.

13 Claims, No Drawings

STABLE AQUEOUS OR AQUEOUS-ALCOHOLIC SOLUTIONS OF FAT-SOLUBLE PERFUME OILS

FIELD OF THE INVENTION

The invention herein relates to stable solutions of fat-soluble perfume oils. More particularly, the invention relates to clear, stable, aqueous or aqueous-alcoholic solutions of fat-soluble perfume oils, which solutions contain hydroxyalkylether alkoxylates as solubilizers.

BACKGROUND OF THE INVENTION

Water soluble perfume oils can often be used for perfuming clear, aqueous or low-percentage alcoholic cosmetics, such as toilet water and shaving and hair lotions. The majority of the ethereal perfumes, perfume oils, and aromatic substances are oil-soluble products, which can be made to stable, clear, aqueous or aqueous-alcoholic solutions only by the addition of what are known as solubilizers. It is already known to use different solubilizers for solubilizing oil-soluble products, such as monofatty acid esters of polyols, examples of which include sorbitol monostearate and various ethylene oxide adducts, such as polyethoxylated castor oil.

A significant drawback of the presently used solubilizers is that relatively large amounts of additives are required to solubilize the desired and/or necessary amounts of perfume oils into a stable, aqueous or low-percentage alcohol solution. Another drawback is that their solubilizing action is mostly very specific and extends only to a limited number of perfume oils.

The problem of finding solubilizers which can in small amounts solubilize a large number of different perfume oils in the desired and necessary concentration to a clear, stable, aqueous or aqueous-alcoholic solution, had already been solved by the use of hydroxyalkylether ethoxylates, as described in German Published Application (DOS) 27 31 218. Although the hydroxyalkylether ethoxylates described in that reference have excellent solubilizing properties for perfume oils, they leave much to be desired as far as their processing capacity is concerned, due to their consistency and partial non-homogeneity, and the products must be melted and homogenized before use.

The problem has therefore been to find solubilizers which have all the application properties of the hydroxyalkylether ethoxylates and which are also clear, liquid, easily processable products, so that stable, aqueous or aqueous-alcoholic solutions of fat-soluble perfume oils may be prepared without any difficulties.

OBJECTS OF THE INVENTION

It is an object of this invention to provide solubilizers for fat-soluble perfume oils.

It is also an object of this invention to provide stable solutions of fat-soluble perfume oils.

It is a further object of this invention to provide solubilizers which in small amounts readily solubilize fat-soluble perfume oils and which are easily processable.

It is a yet further object of this invention to provide stable, aqueous or aqueous-alcoholic solutions of fat-soluble perfume oils which comprise hydroxyalkylether alkoxylates prepared by reacting epoxyalkanes of formula

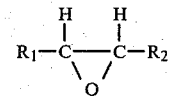

wherein $R_1$ and $R_2$, which can be the same or different, are each hydrogen or an alkyl radical of from about 1 to 24 carbon atoms, with the proviso that the sum of the carbon atoms of $R_1$ and $R_2$ is from about 2 to 26, with monohydric or polyhydric aliphatic alcohols containing from about 1 to 10 carbon atoms and from 1 to 4 hydroxyl groups and then reacting the product obtained successively with propylene oxide and ethylene oxide.

These and other objects of the invention will become more apparent in the discussion below.

DESCRIPTION OF THE INVENTION

The problem of providing suitable solubilizers has been solved by the invention herein. According to the invention, clear, stable, aqueous or aqueous-alcoholic solutions of fat-soluble perfume oils are obtained which have a content of products which are obtained by reacting epoxyalkanes of the formula

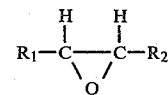

wherein $R_1$ and $R_2$, which can be the same or different, are each hydrogen or an alkyl radical having from about 1 to 24 carbon atoms, with the proviso that the sum of the carbon atoms of $R_1$ and $R_2$ is from about 2 to 26, preferably from about 6 to 20, with monohydric or polyhydric aliphatic alcohols containing from about 1 to 10 carbon atoms and from 1 to 4 hydroxyl groups, in a molar ratio of epoxyalkane to alcohol of from about 1:1.1 to 1:10, preferably from about 1:2 to 1:6, in the absence of solvents and in the presence of from about 0.05 to 10 g per mol of epoxyalkane to be reacted of sulfuric acid or aromatic sulfonic acids with not more than 8 carbon atoms, and at a temperature of from about 50° to 130° C., and then reacting the hydroxyalkylether reaction product obtained, after neutralization of the acid and distialiation of unreacted alcohol, first with from about 0.5 to 10, preferably from about 0.5 to 4 mols, of propylene oxide per mol of ether alcohol, and then with from about 4 to 20 mols, preferably from about 7 to 14 mols, of ethylene oxide. Preferably the molar amount of ethylene oxide exceeds the molar amount of propylene oxide in the product, and especially ratios of ethylene oxide to propylene oxide of from about 4:1 to 12.1 are employed.

Epoxyalkanes can be obtained from corresponding olefins or olefin mixtures by epoxidation according to known methods. The terminal epoxyalkanes, i.e., the 1,2-epoxyalkanes, are obtained from 1,2-monoolefins, which are obtained by, for example, polymerization of ethylene with organic aluminum compounds as catalysts or thermal cracking of paraffinhydrocarbons. Examples of preferred epoxyalkanes include the compounds 1,2-epoxydodecane, 1,2-epoxytetradecane, 1,2-epoxyhexadecane, 1,2-epoxyoctadecane and epoxide mixtures, such as $C_{12/14}$-1,2-epoxide with about 70% by weight of $C_{12}$-epoxyalkane and about 30% by weight of $C_{14}$-epoxyalkane, or $C_{16/18}$-1,2-epoxide with about 40% by weight of $C_{16}$-epoxyalkane and about 60% by weight of $C_{18}$-epoxyalkane.

The non-terminal epoxyalkanes, i.e., the epoxyalkanes having the epoxy moiety at a position other than 1,2, are obtined, for example, by epoxidation of non-terminal olefins or olefin mixtures, such compounds or mixtures being prepared by catalytic dehydrogenation or by chlorination/dehydrochlorination of linear paraffin hydrocarbons. Monolefins with non-terminal double bonds can also be obtained by isomerization of α-olefins. Preferred non-terminal epoxyalkanes from a $C_{11/14}$-olefin fraction contain about 22% by weight of $C_{11}$-epoxyalkane, about 30% by weight of $C_{12}$-epoxyalkanes, about 26% by weight of $C_{13}$-epoxyalkane, and about 22% by weight of $C_{14}$-epoxyalkane. A similarly suitable mixture of non-terminal epoxyalkanes of a $C_{15/18}$-olefin fraction contains about 26% by weight of $C_{15}$-epoxyalkane, about 35% by weight of $C_{16}$-epoxyalkane, about 32% by weight of $C_{17}$-epoxyalkane, and about 7% by weight of $C_{18}$-epoxyalkane.

Suitable monohydric or polyhydric aliphatic alcohols, which contain from about 1 to 10 carbon atoms and from 1 to 4 hydroxyl groups, include, for example, alkanols having from 1 to 10 carbon atoms such as methanol, ethanol, n-buta-nol, n-hexanol, ethyl hexanols, n-octanol; alkanediols having from 2 to 10 carbon atoms such as ethanediol-1,2, propanediol-1,2; alkanetrils having from 3 to 10 carbon atoms such as glycerin; and 1,1,1-tris(hydroxymethyl)-propane, also known as trimethylol propane. Ethanediol-1,2 is of particular importance.

If the supply of monohydric or polyhydric alcohols in the reaction mixture is high, i.e., if the epoxyalkane to alcohol molar ratio is about 1:2 or above, the reaction product will have a high portion of reaction products from 1 mol of epoxyalkane with 1 mol of alcohol. With a lower alcohol supply, i.e., an epoxyalkane to alcohol molar ratio of less than about 1:2, secondary reaction products will be formed increasingly from 1 mol of epoxyalkane with 1 mol of reacted ether alcohol. Advantageously the epoxyalkane to alcohol molar ratio will be from about 1:2 to 1:6, and the portion of primary reaction products in the reaction mixture will be from about 70 to over 99 mol percent, based on the theoretically possible yield.

The amount of strong acids to be used as catalysts depends to a certain extent on the type of epoxyalkane and alcohol. In general, from about 0.05 to 10 g of acid per mol of the epoxyalkane to be reacted, is employed, which results in a high reaction rate.

Sulfuric acid is a catalytically strong acid which leads to light-colored to colorless products with a high activity under the conditions of the method disclosed herein without any marked corrosion in the parts of the equipment. A complete reaction can be achieved within about 1 to 5 hours, and the completeness of the reaction can be checked by measuring the epoxide number or by gas chromatograph. Similar results are obtained with the use of aromatic hydrocarbon sulfonic acids having no more than 8 carbon atoms such as, for example, benzene-sulfonic acid, xylene-sulfonic acid, and especially p-toluene-sulfonic acid. Particularly light-colored reaction products are obtained if the reaction is carried out at reaction temperatures of from about 70° to 90° C. After the reaction is complete, the acid used as a catalyst is neutralized. In principle all strong inorganic bases, such as NaOH, KOH, or LiOH or organic bases, such as alkali metal alcoholates or quaternary ammonium bases, can be used for this purpose. Sodium methylate is particularly suitable.

Excess alcohol is separated after the neutralization of the acid by distillation under reduced pressure, the distillation temperature being maintained at a temperature that doesn't exceed 150° C. If the distillation temperature is higher, the reaction products are discolored. Dependent upon the duration of action of the temperature on the reaction mixture, it may be advisable for the production of light-colored products to separate the alcohol by reducing the distillation pressure, even at distillation temperatures lower than 150° C.

The ether alcohols obtained are reacted according to known methods in an autoclave at reaction temperatures of from about 160° to 180° C. in the presence of sodium methylate as a catalyst with the desired amounts of propylene oxide and then ethylene oxide. The end products obtained represent clear liquids which do not turn cloudy, even at low temperatures.

Of particular importance as solubilizers in the clear, aqueous or aqueous-alcoholic solutions of fat-soluble perfume oils are the products derived from terminal $C_{12}$–$C_{14}$-, $C_{12}$–$C_{18}$-, $C_{14}$–$C_{16}$-, or $C_{15}$–$C_{18}$-epoxyalkanes and the products obtained from non-terminal $C_{15}$–$C_{18}$-epoxyalkanes by reaction with ethanediol-1,2.

Preferred compounds are reaction product of

α-$C_{14/16}$-epoxide+glycol+1 propylene oxide (PO)+9 ethylene oxide (EO);
α-$C_{12/18}$-epoxide+glycol+1.2 PO+9 EO;
α-$C_{12/14}$-epoxide+glycol+1 PO+10 EO;
α-$C_{16/18}$-epoxide+glycol+1 PO+11 EO;
α-$C_{14/16}$epoxide+glycol+1.2 PO+9 EO;
i-$C_{15/18}$-epoxide+glycol+1 PO+9 EO; and
i-$C_{15/18}$-epoxide+glycol+1.2 PO+9 EO, where "glycol" is ethylene glycol and "i" designates a non-terminal epoxy group.

Useful fat-soluble perfume oils include natural or synthetic ethereal oils of all types, such as orange oil, designorange oil, pine oil, peppermint oil, eucalyptus oil, lemon oil, clove leaves oil, cedar wood oil, bergamot oil, rosemary oil, patchouli oil, lavandin oil, oil of spike, rose oil, vetiver oil, oil of fennel, anise oil, thymian oil, geranium oil, lavender oil, menthol, as well as synthetic oil-soluble perfume oils selected from the group consisting of the aldehydes, esters and polyene-compounds.

The quantitative ratios of fat-soluble perfume oil and hydroxyalkylether alkoxylate in the clear, stable, aqueous or aqueous-alcoholic solutions according to the invention can vary greatly and depend on the type of perfume oil, on the type of solubilizers, on the alcohol content, and other accompanying substances which are present in the solution.

The hydroxyalkylether alkoxylates can be present in the solutions in amounts of from about 0.1 to 20% by weight, preferably in amounts of from about 0.5 to 5% by weight, based on the weight of the total solution. The desired amounts of perfume should not be substantially above or below the limits of 0.1 to 1% by weight, i.e., the amounts should be from about 0.05 to 2% by weight.

The clear, stable, aqueous or aqueous-alcoholic solutions of fat-soluble perfume oils can be produced in known manner by mixing corresponding concentrates of perfume oil and hydroxyalkylether alkoxylate in the desired ratio with water or an alcohol-water mixture.

The following examples are intended to illustrate the subject of the invention and are not to be construed as limiting the invention thereto.

EXAMPLES

PREPARATION OF HYDROXYALKYLETHER ALKOXYLATES (a) α-$C_{12/18}$-epoxide+glycol+1.2 PO+9 EO (5% $C_{12}$, 35% $C_{14}$, 60% $C_{16/18}$)

An amount of 1066 g of a mixture of 5% α-$C_{12}$-, 35% α-$C_{14}$-, 24% α-$C_{16}$ and 36% α-$C_{18}$-epoxide was added dropwise to 1315 g of ethylene glycol which had been mixed with 1.1 g of conc. sulfuric acid and heated to 70°–75° C. The temperature was kept at between 75° and 80° C. during the reaction by supplying epoxide or by cooling, if necessary. After the reaction of the epoxide, the catalyst was neutralized with 3.5 g of sodium methylate (30% solution in methanol), in the excess glycol was distilled off in vacuo. An amount of 1525 g of ether alcohol was obtained.

Four hundred sixteen grams of the ether alcohol were mixed with 7.9 g of sodium methylate (30% solution in methanol) as catalyst, and reacted in an autoclave first with 87.5 g of propylene oxide and then with 496.5 g of ethylene oxide at reaction temperature 160° and 180° C. The maximum pressure applied was 4.5 bar. One thousand grams of alkoxylate were obtained.

In a similar manner, the following hydroxyalkylether alkoxylates were prepared:

(b) α-$C_{12/18}$-epoxide+glycol+1.2 PO+9 EO (10% $C_{12}$, 30% $C_{14}$, 60% $C_{16/18}$);
(c) α-$C_{14/18}$-epoxide+glycol+1 PO+9 EO;
(d) α-$C_{12/14}$-epoxide+trimethylol propane+1 PO+10 EO;
(e) α-$C_{16/18}$-epoxide+trimethylol propane+1 PO+11 EO;
(f) i-$C_{11/14}$-epoxide+glycol+1.2 PO+9 EO; and
(g) α-$C_{12/14}$-epoxide+glycol+1 PO+9 EO.

TESTING

A 1% aqueous solution of perfume was employed for testing purposes. To prepare such a solution, one of the perfume oils indicated below was first stirred with the respective solubilizer in a certain quantitative ratio, and then water sufficient to make a 1% solution, based on weight of the total perfume solution, was added. The ratios of solubilizer to perfume oil were selected as 7:3 and 8:2, respectively, which correspond to about two- to four-fold amounts of solubilizer per perfume oil.

The following ten ethereal oils of varying composition and polarity were used as test substances:

| (01) rosemary oil | (06) orange oil |
|---|---|
| (02) bergamot oil | (07) pine oil |
| (03) cedar wood oil | (08) peppermint oil |
| (04) clove leaves oil | (09) patchouli oil |
| (05) lemon oil | (10) lavandin oil |

The aqueous solutions of perfume oil were visually evaluated to ascertain solubility characteristics. The results of the evaluations are set forth in the table below, where x=cloudy solution, xx=weakly clouded solution, and xxx=clear, stable solution.

TABLE

| Solubilizer | Sol:Oil Ratio | 01 | 02 | 03 | 04 | 05 | 06 | 07 | 08 | 09 | 010 | Wt. of Dissolved Oils |
|---|---|---|---|---|---|---|---|---|---|---|---|---|
| a | 7:3 | xxx | xx | x | xxx | xx | xxx | xxx | x | x | x | |
|   | 8:2 | xxx | xxx | xxx | xxx | xxx | xxx | xxx | xxx | xxx | xxx | 10 |
| b | 7:3 | xxx | x | x | xx | xx | xxx | xxx | x | x | x | |
|   | 8:2 | xxx | xxx | xxx | xxx | xxx | xxx | xxx | xxx | xxx | xxx | 10 |
| c | 7:3 | xxx | xxx | xx | xxx | xx | xxx | xxx | x | x | xx | |
|   | 8:2 | xxx | xxx | xxx | xxx | xxx | xxx | xxx | xxx | xxx | xxx | 10 |
| d | 7:3 | x | x | x | x | x | x | xxx | x | x | x | |
|   | 8:2 | xx | xxx | x | xxx | xx | xxx | xxx | xx | xx | xx | 4 |
| e | 7:3 | x | x | x | xxx | x | x | x | x | x | xxx | |
|   | 8:2 | xxx | xxx | xx | xxx | xx | xxx | xxx | xxx | xx | xxx | 7 |
| f | 7:3 | xx | xx | x | xx | xx | xx | xxx | x | xx | x | |
|   | 8:2 | xxx | xxx | xx | xxx | xxx | xxx | xxx | xx | xxx | xx | 7 |
| g | 7:3 | xxx | x | x | xx | xx | xx | xx | x | x | x | |
|   | 8:2 | xxx | xxx | xxx | xxx | xxx | xxx | xxx | xxx | xxx | xxx | 9 |

The table also indicates how many oils a solubilizer can dissolve. The more oils a solubilzer can dissolve, the better it is considered as a solubilizer, since it can be used more generally. The results indicated in the table can naturally be improved by a high ratio solubilizer: perfume oil.

The preceding specific embodiments are illustrative of the practice of the invention. It is to be understood, however, that other expedients known to those skilled in the art or disclosed herein may be employed without departing from the spirit of the invention, or the scope of the appended claims.

We claim:

1. A clear, stable, aqueous or aqueous-alcoholic solution of a fat-soluble perfume oil, which comprises
   (a) from about 0.1 to 20% by weight, based on the total weight of the solution, of a hydroxyalkylether alkoxylate prepared by reacting an epoxyalkane of the formula

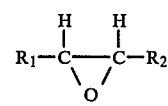

wherein $R_1$ and $R_2$, which may be the same or different, each represent hydrogen or an alkyl radical having from about 1 to 24 carbon atoms, with the proviso that the sum of the carbon atoms in $R_1$ and $R_2$ is from about 2 to 26, or a mixture thereof, with monohydric or polyhydric aliphatic alcohols having from 1 to 10 carbon atoms and from 1 to 4 hydroxyls groups in molar ratio of epoxyalkane to alcohol of from 1:1.1 to 1:10 in the absence of solvents and in the presence of from about 0.25 to 10 g per mol of epoxyalkane of sulfuric acid or aromatic sulfonic acid not having more than 8 carbon atoms at from about 50° to 130° C., to form an ether alcohol, and then, after neutralization of the acid and distillation of unreacted alcohol, reacting the ether alcohol obtained first with from about 0.5 to 10 mols of propylene oxide per mol of ether alcohol and then with from about 4 to 20 mols of ethylene oxide per mol of ether alcohol, the molar ratio of the ethylene oxide employed to the propylene oxide employed being from about 4:1 to 12:1;

(b) from about 0.1 to 1.0% by weight, based on the total weight of the solution, of a fat-soluble perfume oil; and (c) the remainder to 100% by weight of water or water and a water-miscible alcohol.

2. The solution of claim 1 wherein the sum of the carbon atoms of $R_1$ and $R_2$ is from about 6 to 20.

3. The solution of claim 1 wherein the molar ratio of epoxyalkane to alcohol is from about 1:2 to 1:6.

4. The solution of claim 1 wherein the ether alcohol is reacte with from about 0.5 to 4 mols of propylene oxide per mol of ether alcohol.

5. The solution of claim 1 wherein the ether alcohol is reacted with from about 7 to 14 mols of ethylene oxide per mol of ether alcohol.

6. The solution of claim 1 wherein the epoxyalkane is reacted with ethylene glycol in a molar ratio of epoxyalkane to ethylene glycol of from about 1:2 to 1:6 to form an ether alcohol, and then the ether alcohol is reacted with from about 0.5 to 4 mols of propylene oxide per mol of ether alcohol and from about 7 to 14 mols of ethylene oxide per mol of ether alcohol.

7. The solution of claim 1 which contains other conventional substances present in aqueous or aqueous-alcoholic solutions of fat-soluble perfume oils.

8. The solution of claim 1, wherein the epoxyalkane is 1,2-epoxydodecane, 1,2-epoxytetradecane, 1,2-epoxyhexadecane, 1,2-epoxyoctadecane, a mixture comprising about 70% by weight of $C_{12}$-1,2-epoxyalkane and about 30% by weight of $C_{14}$-1,2-epoxyalkane, or a mixture comprising about 40% by weight of $C_{16}$-1,2-epoxyalkane and about 60% by weight of $C_{18}$-1,2-epoxyalkane.

9. The solution of claim 1, wherein the epoxyalkane is a mixture of non-terminal epoxyalkanes comprising a mixture of about 22% by weight of $C_{11}$-epoxyalkane, about 30% by weight of $C_{12}$-epoxyalkane, about 26% by weight of $C_{13}$-epoxyalkane, and about 22% by weight of $C_{14}$-epoxyalkane or a mixture of about 26% by weight of $C_{15}$-epoxylalkane, about 35% by weight of $C_{16}$-epoxyalkane, about 32% by weight of $C_{17}$-epoxyalkane, and about 7% by weight of $C_{18}$-epoxyalkane.

10. The solution of claim 1, wherein the hydroxyalkylether alkoxylate (a) is the product of reaction from a member selected from the group consisting of:

α-$C_{14/16}$-epoxide+ethylene glycol+1 PO+9 EO;
α-$C_{12/18}$-epoxide+ethylene glycol+1.2 PO+9 EO;
α-$C_{12/14}$-epoxide+ethylene glycol+1 PO+10 EO;
α-$C_{16/18}$-epoxide+ethylene glycol+1 PO+11 EO;
α-$C_{14/16}$-epoxide+ethylene glycol+1.2 PO+9 EO;
i-$C_{15/18}$-epoxide+ethylene glycol+1 PO+9 EO; and
i-$C_{15/18}$-epoxide+ethylene glycol+1.2 PO+9 EO.

11. The solution of claim 1, wherein the ratio of component (a) to component (b) is from about 2:1 to 4:1.

12. The solution of claim 1 which comprises from about 0.5 to 5% by weight, based on the total weight of the solution, of hydroxyalkylether alkoxylate.

13. A method of solubilizing a fat-soluble perfume oil in a clear, stable, aqueous or aqueous-alcoholic solution comprising adding water or an alcohol-water mixture to a concentrate of said perfume oil and a hydroxyalkylether alkoxylate prepared by reacting an epoxyalkane of the formula

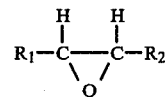

wherein $R_1$ and $R_2$, which may be the same or different, each represent hydrogen or an alkyl radical having from about 1 to 24 carbon atoms, with the proviso that the sum of the carbon atoms in $R_1$ and $R_2$ is from about 2 to 26, or a mixture thereof, with monohydric or polyhdyric aliphatic alcohols having from about 1 to 10 carbon atoms and from 1 to 4 hydroxyl groups in molar ratio of epoxyalkane to alcohol of from 1:1.1 to 1:10 in the absence of solvents and in the presence of from about 0.25 to 10 g per mol of epoxyalkane of sulfuric acid or aromatic sulfonic acid not having more than 8 carbon atoms at from about 50° to 130° C., to form an ether alcohol, and then, after neutralization of the acid and distillation of unreacted alcohol, reacting the ether alcohol obtained first with from about 0.5 to 10 mols of propylene oxide per mol of ether alcohol and then with from about 4 to 20 mols of ethylene oxide per mol of ether alcohol, the molar ratio of the ethylene oxide employed to the propylene oxide employed being from about 4:1 to 12:1.

* * * * *

UNITED STATES PATENT AND TRADEMARK OFFICE
CERTIFICATE OF CORRECTION

PATENT NO. : 4,299,737

DATED : November 10, 1981

INVENTOR(S) : ALFRED MEFFERT et al.

It is certified that error appears in the above—identified patent and that said Letters Patent is hereby corrected as shown below:

Column 2, line 46: "distiallation" should read -- distillation --.

Column 2, line 47: "10" should read -- 10 mols --.

Column 3, line 5: "obtined" should read -- obtained --.

Column 3, line 25: "n-buta-nol" should read -- n-butanol --.

Column 3, line 28: "trils" should read -- triols --.

Column 4, line 40: delete "designorange oil".

Column 5, line 37: "in the" should read -- and the --.

Column 5, line 44: "temperature" should read -- temperatures between --.

Column 7, line 21: "reacte" should read -- reacted --.

Column 8, line 36: "polyhdyric" should read -- polyhydric --.

Signed and Sealed this

Thirty-first Day of August 1982

[SEAL]

Attest:

Attesting Officer

GERALD J. MOSSINGHOFF

Commissioner of Patents and Trademarks